US009830524B2

(12) United States Patent
Sekiguchi et al.

(10) Patent No.: US 9,830,524 B2
(45) Date of Patent: Nov. 28, 2017

(54) METHOD FOR ESTIMATING SHAPE BEFORE SHRINK AND CD-SEM APPARATUS

(75) Inventors: Tomoko Sekiguchi, Tokyo (JP); Takeyoshi Ohashi, Tokyo (JP); Junichi Tanaka, Tokyo (JP); Zhaohui Cheng, Tokyo (JP); Ruriko Tsuneta, Tokyo (JP); Hiroki Kawada, Tokyo (JP); Seiko Hitomi, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 484 days.

(21) Appl. No.: 14/239,803

(22) PCT Filed: May 24, 2012

(86) PCT No.: PCT/JP2012/063324
§ 371 (c)(1),
(2), (4) Date: Apr. 28, 2014

(87) PCT Pub. No.: WO2013/027453
PCT Pub. Date: Feb. 28, 2013

(65) Prior Publication Data
US 2015/0036914 A1    Feb. 5, 2015

(30) Foreign Application Priority Data
Aug. 22, 2011 (JP) ................. 2011-180385

(51) Int. Cl.
*G01N 23/22* (2006.01)
*G06K 9/46* (2006.01)
(Continued)

(52) U.S. Cl.
CPC ........... *G06K 9/4604* (2013.01); *B82Y 10/00* (2013.01); *B82Y 40/00* (2013.01); *G01B 15/04* (2013.01);
(Continued)

(58) Field of Classification Search
None
See application file for complete search history.

(56) References Cited

U.S. PATENT DOCUMENTS

| 7,816,062 B2 | 10/2010 | Nagatomo et al. |
| 9,305,744 B2 * | 4/2016 | Ohashi .................. G01B 15/04 |

(Continued)

FOREIGN PATENT DOCUMENTS

| JP | 2005-057037 A | 3/2005 |
| JP | 2005-331524 A | 12/2005 |

(Continued)

OTHER PUBLICATIONS

Bunday et al., "Phenomenology of electron-beam-induced photoresist shrinkage trends" SPIE 7272, Metrology, Inspection, and Process Control for Microlithography XXIII, (Mar. 24, 2009).*
(Continued)

*Primary Examiner* — Jason McCormack
*Assistant Examiner* — James Choi
(74) *Attorney, Agent, or Firm* — Miles & Stockbridge P.C.

(57) ABSTRACT

In the present invention, at the time of measuring, using a CD-SEM, a length of a resist that shrinks when irradiated with an electron beam, in order to highly accurately estimate a shape and dimensions of the resist before shrink, a shrink database with respect to various patterns is previously prepared, said shrink database containing cross-sectional shape data obtained prior to electron beam irradiation, a cross-sectional shape data group and a CD-SEM image data group, which are obtained under various electron beam irradiation conditions, and models based on such data and data groups, and a CD-SEM image of a resist pattern to be measured is obtained (S102), then, the CD-SEM image and data in the shrink database are compared with each other
(Continued)

(S103), and the shape and dimensions of the pattern before the shrink are estimated and outputted (S104).

13 Claims, 9 Drawing Sheets

(51) Int. Cl.
| | | |
|---|---|---|
| H01J 37/317 | (2006.01) | |
| G01B 15/04 | (2006.01) | |
| B82Y 10/00 | (2011.01) | |
| B82Y 40/00 | (2011.01) | |
| G06T 7/00 | (2017.01) | |
| H01L 21/66 | (2006.01) | |

(52) U.S. Cl.
CPC ........... *G01N 23/22* (2013.01); *G06T 7/0004* (2013.01); *H01J 37/3174* (2013.01); *H01J 2237/221* (2013.01); *H01J 2237/226* (2013.01); *H01J 2237/2816* (2013.01); *H01J 2237/31754* (2013.01); *H01J 2237/31796* (2013.01); *H01L 22/12* (2013.01); *H01L 2924/0002* (2013.01)

(56) References Cited

U.S. PATENT DOCUMENTS

| | | | | |
|---|---|---|---|---|
| 9,316,492 | B2* | 4/2016 | Peterson | G01B 15/04 |
| 2005/0247876 | A1* | 11/2005 | Kawada | G01B 15/00 |
| | | | | 250/310 |
| 2006/0060774 | A1 | 3/2006 | Oosaki et al. | |
| 2007/0093044 | A1* | 4/2007 | Rijpers | C23C 16/047 |
| | | | | 438/584 |
| 2007/0105243 | A1* | 5/2007 | Nagatomo | H01L 22/12 |
| | | | | 438/14 |
| 2007/0288177 | A1* | 12/2007 | Rothenfusser | G01N 25/72 |
| | | | | 702/40 |
| 2008/0179517 | A1* | 7/2008 | Kawada | B82Y 15/00 |
| | | | | 250/307 |
| 2009/0197189 | A1* | 8/2009 | Ide | G03F 7/70641 |
| | | | | 430/30 |
| 2009/0224152 | A1 | 9/2009 | Shishido et al. | |
| 2009/0263024 | A1 | 10/2009 | Yamaguchi et al. | |
| 2010/0038535 | A1 | 2/2010 | Nasu et al. | |
| 2012/0298865 | A1* | 11/2012 | Omori | G03F 7/70625 |
| | | | | 250/310 |
| 2014/0048706 | A1* | 2/2014 | Kawada | G01B 15/06 |
| | | | | 250/307 |

FOREIGN PATENT DOCUMENTS

| | | |
|---|---|---|
| JP | 2005-338102 A | 12/2005 |
| JP | 2006-093251 A | 4/2006 |
| JP | 2006-138864 A | 6/2006 |
| JP | 2007-120968 A | 5/2007 |
| JP | 2007-129059 A | 5/2007 |
| JP | 2009-257937 A | 11/2009 |
| JP | 2012-173225 A | 9/2012 |
| JP | 2013-083466 A | 5/2013 |
| WO | WO 2012/114411 A1 | 8/2012 |
| WO | WO 2013/051456 A1 | 4/2013 |

OTHER PUBLICATIONS

Bunday et al. "Phenomenology of electron-beam-induced photoresist shrinkage trends" Proceedings of SPIE—The International Society for Optical Engineering (Mar. 2009).*

* cited by examiner

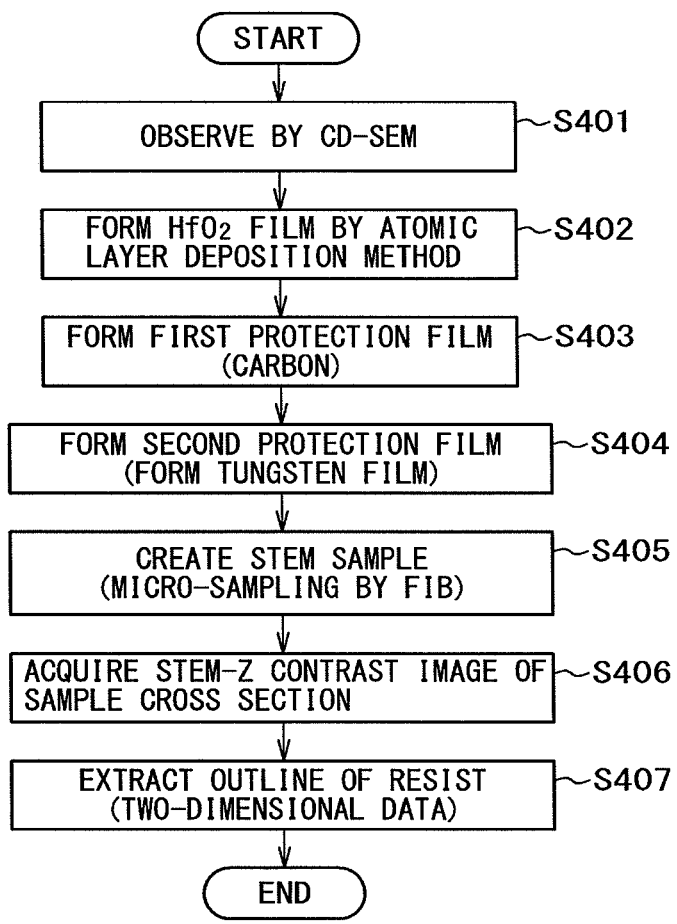

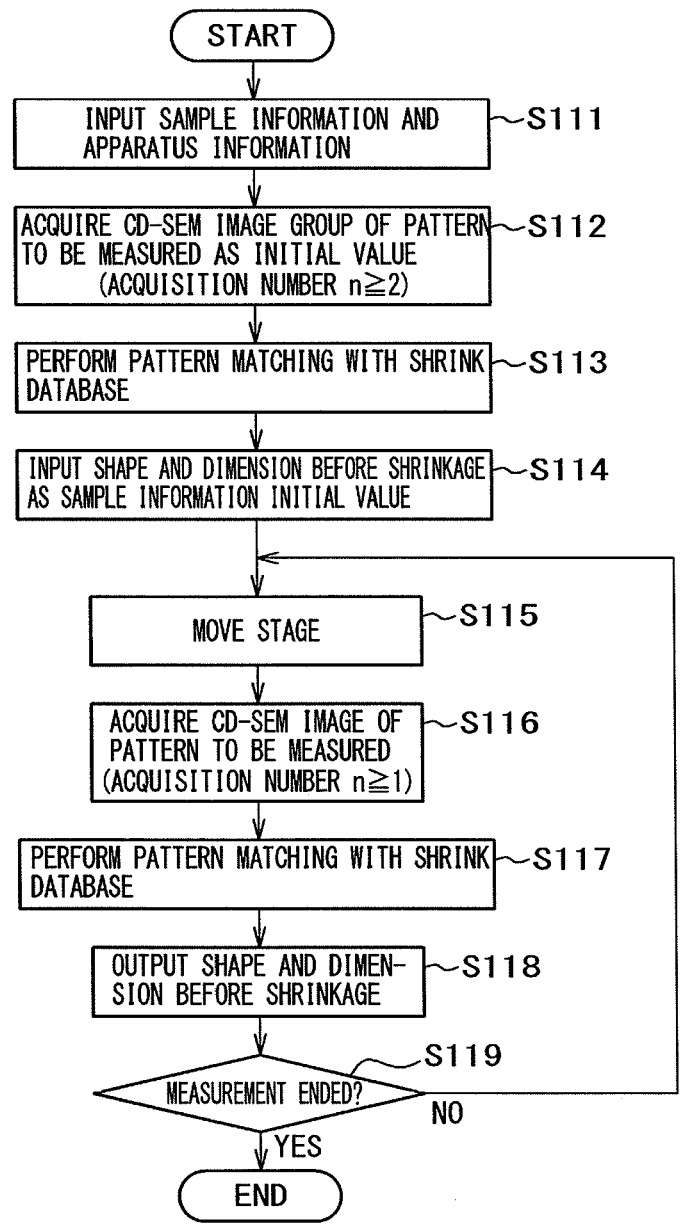

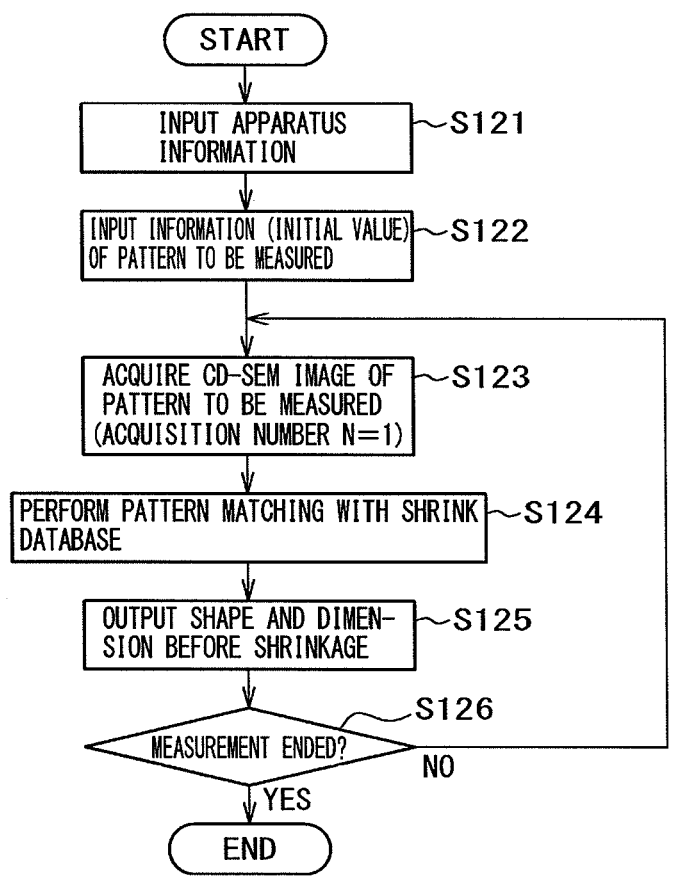

METHOD FOR ESTIMATING SHAPE BEFORE SHRINK AND CD-SEM APPARATUS

TECHNICAL FIELD

The present invention relates to a method for estimating a shape before shrink and a CD-SEM apparatus.

BACKGROUND ART

On the ground of slow practical application of EUV (Extreme Ultra Violet) lithography as the next generation technology, an ArF liquid immersion exposure technique has been demanded to be the technique that leads to the next generation which is designed to expose around the resolution limit.

For this, an OPC (Optical Proximity Correction) in consideration of the proximity effect of light for the mask pattern correction has become an essential technique. In the OPC process, the actually transferred mask pattern has to be measured and corrected. Especially, it is important to measure the length of the specific point where the defect is likely to occur in the exposure pattern called hot spot. The importance of pattern dimension management using a CD-SEM (Critical Dimension-Scanning Electron Microscope) has been increasingly focused.

In measuring the ArF resist using the CD-SEM, the resist shrinks under the electron beam irradiation. Therefore, it is necessary to obtain the accurate shrink quantity for achievement of highly accurate length measurement.

The cross-sectional shape of the resist gives a great influence on the shape of the resist in the next process where the resist is processed into the mask. For example, trailing or constriction generated in the side wall of the resist may deteriorate accuracy of the processing dimensions. Accordingly, the need of measuring the cross-sectional shape of the resist has been increasingly demanded as well as the width dimension.

As the method for estimating the shrink quantity of the resist upon measurement using the CD-SEM, the method disclosed in Patent Literature 1 is known. The method is designed to derive the relationship (shrink curve) between the number of measurements of the resist pattern width using the CD-SEM multiple times and a change amount of the resist pattern width (shrink curve) so as to calculate the shrink quantity.

Patent Literature 2 discloses the method for obtaining information of the cross-sectional shape using an SEM image, for example. The method disclosed in Patent Literature 2 is designed to calculate image feature amount effective for estimating a cross-sectional shape of an evaluated pattern, a process condition, and a device characteristic from the SEM image of the evaluated pattern in the exposure process or the etching process. The image feature amount is subjected to a matching process with learning data for associating the cross-sectional shape of the pattern, the process condition, and the device characteristic which are preliminarily stored in the database with the image feature amount calculated from the SEM image so that the cross-sectional shape of the evaluated pattern, the process condition, and the device condition are calculated.

CITATION LIST

Patent Literature

Patent Literature 1: JP-A-2005-57037
Patent Literature 2: JP-A-2007-129059

SUMMARY OF INVENTION

Technical Problem

The inventors obtain the shrink quantity through the method as disclosed in Patent literature 1 to discover a large error in a fine pattern dimension as the property that will become necessary in future. Then the cause of such error was examined to find out the large estimated error of the shrink quantity resulting from the method using the shrink curve for estimating the shrink quantity as disclosed in Patent Literature 1 through measurement of the resist pattern multiple times as described below. Deformations of the resist and an antireflection film proceed, and the resist height changes as increase in the number of measurements of the resist width. Then the measurement position of the resist width to be measured at the resist height also changes accordingly. Specifically, if the number of measurements is small, the measurement is conducted at the position half the height of the resist. However, as the number of measurements increases, the measurement position shifts to reach the point at the upper part of the resist (¾ of the height, for example).

As the observation of the pattern with the CD-SEM is conducted from above, it is difficult to measure the cross-sectional shape.

The shrink of the resist upon acquisition of the CD-SEM image is not considered in the estimation method using the database of the CD-SEM image and the cross-sectional shape as disclosed in Patent Literature 2. As the CD-SEM images that constitute the database are derived from irradiation of electron beam when acquiring the image, the resist shape after shrink is obtained. Meanwhile, the cross-sectional shape derived from analysis of the cross-sectional SEM and AFM (Atomic Force Microscope), and the cross-sectional shape derived from the lithography simulator which constitute the database result in the one before electron beam irradiation rather than at the observed point with the CD-SEM, that is, before shrink. This is caused by the difficulty in direct observation of the cross-sectional shape of the region observed with the CD-SEM by reason of the fine resist pattern, the region too small to be observed by the CD-SEM, weakness of the resist in the electron beam and heat. In the case where the shrinkable material such as the resist is subjected to the measurement, the CD-SEM image and the cross-sectional shape which constitute the database do not provide the data derived from measuring the same shape. Accordingly, it is difficult to conduct the accurate estimation.

An object of the present invention is to provide a method for estimating a shape before shrink and a CD-SEM apparatus, capable of estimating the dimension of the pattern before shrink with high accuracy upon measurement of the shape and dimension of the pattern formed of the material which shrinks under the electron beam irradiation.

Solution to Problem

The following structure is employed for the purpose of solving the aforementioned problem.

The present invention includes various types of means for solving the problem, for example, the method for estimating shape before shrink of a pattern is used for measuring a shape and a dimension of the pattern formed of a substance which shrinks under an electron beam irradiation using a CD-SEM. The method includes the steps of preparing a shrink database which includes cross-sectional shape data of the pattern formed of the substance before the electron beam irradiation, a cross-sectional shape data group obtained under various electron beam irradiation conditions, a CD-SEM image data group obtained under various electron beam irradiation conditions, a shrink model generated by using those data, and a correlation model between a CD-SEM image feature amount and a cross-sectional shape, acquiring the CD-SEM image of a measured pattern formed of the substance, and estimating and outputting the shape and the dimension of the measured pattern before shrink using the CD-SEM image and data of the shrink database.

The CD-SEM apparatus is provided with an electron beam source, a sample stage on which a measured sample is disposed, an electron optical system for irradiating the sample on the sample stage with an electron emitted from the electron beam source, and a control process unit for executing an image processing based on a secondary electron discharged from the sample. The CD-SEM apparatus further includes a shrink database which includes cross-sectional shape data of a pattern formed of a substance which shrinks under an electron beam irradiation, a cross sectional shape data group obtained under various electron beam irradiation conditions, a CD-SEM image data group obtained under various electron beam irradiation conditions, a shrink model generated using those data, and a correlation model between a CD-SEM image feature amount and a cross-sectional shape for estimating the shape of the pattern formed of the substance before shrink.

Advantageous Effects of Invention

The present invention provides a method for estimating a shape before shrink and a CD-SEM apparatus, capable of estimating the dimension of the pattern before shrink with high accuracy using the shrink database upon measurement of the shape and dimension of the pattern formed of the substance which shrinks under electron beam irradiation.

Any other problem, structure and advantageous effect will be made clear by the explanation of the following embodiments.

BRIEF DESCRIPTION OF DRAWINGS

FIG. 4 is a flowchart representing a method for observing the cross-sectional shape of the pattern at the CD-SEM observation point through the method for estimating the shape before shrink according to the first embodiment of the present invention.

FIG. 7 is a flowchart representing the method for estimating a shape before shrink according to a second embodiment of the present invention.

FIG. 8 is a flowchart representing the method for estimating a shape before shrink according to a third embodiment of the present invention.

DESCRIPTION OF EMBODIMENTS

Embodiments according to the present invention will be described based on the drawings.

First Embodiment

Figure 2:
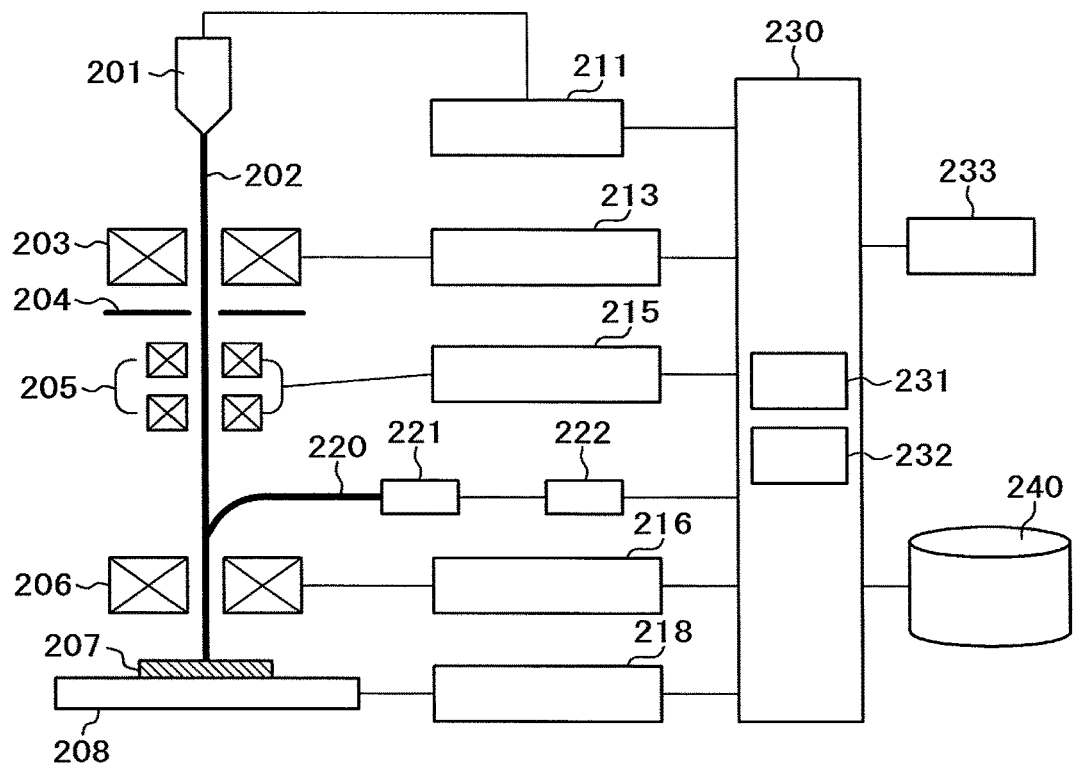
FIG. 2 is a schematic view illustrating an overall structure of a CD-SEM apparatus according to the first embodiment of the present invention.

FIG. 2 illustrates an exemplary structure of the CD-SEM apparatus according to the embodiment. A predetermined accelerating voltage set by a high voltage control unit 211 is discharged, and a primary electron 202 of current is emitted from an electron gun 201. The emitted primary electron 202 of the current is converged by a condenser lens 203 controlled by a condenser lens control unit 213 so that the unnecessary region of the primary electron 202 is removed through a aperture 204.

Thereafter, the primary electron 202 is converged on a sample 207 by an objective lens 206 controlled by an objective lens control unit 216 for scanning on the sample 207 using a deflection coil 205 controlled by a deflection coil control unit 215. The sample 207 is fixed on a stage 208, movement of which is controlled by a stage control unit 218. This ensures to irradiate an arbitrary point on the sample 207 with the primary electron 202.

A secondary electron 220 generated from the sample 207 by irradiation of the primary electron 202 is detected by a secondary electron detector 221, converted into a digital signal by an A/D converter 222, and stored in a memory 232 within a control process unit 230 so that an image processing suitable for the object is executed by a CPU 231, for example, the line profile is acquired.

The control process unit 230 includes the CPU 231 and the memory 232. The control process unit 230 controls the respective control units such as the high voltage control unit 211, the condenser lens control unit 213, the deflection coil control unit 215, the objective lens control unit 216, and the stage control unit 218 to set arbitrary measurement conditions such as the accelerating voltage, current, scanning speed, the number of scanning operations, magnification, and the measurement point on the sample 207. The measurement conditions and measurement point are stored in the memory 232 of the control process unit 230 together with the CD-SEM images of the measured secondary electron 220.

A data input/output unit 233 connected to the control process unit 230 serves to connect the control process unit 230 to an operator. The operator executes the control of the respective parts as described above through the input from the data input/output unit 233. The aforementioned measurement conditions and measurement points may be set through the data input/output unit 233. The primary electron 202 is two-dimensionally scanned on the sample 207, and the generated secondary electron signals are controlled by the control process unit 230 in a two-dimensional arrangement corresponding to the scanning position. This makes it possible to output and display the two-dimensional image (CD-SEM image) corresponding to the surface shape of the specimen (sample) from the data input/output unit 233. This also makes it possible to obtain the feature amount of the CD-SEM image such as the line spectrum by the CPU 231 from the obtained two-dimensional CD-SEM image.

A shrink database 240 connected to the control process unit 230 is formed based on preliminarily measured CD-SEM images each with a pattern formed of the material shrinkable under the electron beam irradiation, and images of a scanning transmission electron microscope (STEM) as a cross-section of the pattern point corresponding to the CD-SEM image. This database is used for estimating the pattern shape from the CD-SEM image before shrink, the details of which will be described later. FIG. 2 illustrates the shrink database 240 as a unit provided separately from the control process unit 230. The similar effect may be obtained by the shrink database 240 configured to contain the control process unit 230.

The CD-SEM image of the pattern formed on the sample acquired using the CD-SEM apparatus shown in FIG. 2 is subjected to an analytical process by the CPU 231 of the control process unit 230 based on the shrink database 240. This makes it possible to estimate the pattern shape from the CD-SEM image before shrink, and allows the data input/output unit 233 to output the pattern shape and the dimension. The shape and dimension of the pattern to be outputted may be designated through the input from the data input/output unit 233.

In measuring the pattern shape with the CD-SEM, the electron beam irradiation applied to the pattern formed on the sample is unavoidable. Accordingly, the CD-SEM image of the pattern formed of the material shrinkable under the electron beam irradiation is derived from measurement of the shape after shrink. The CD-SEM image after shrink is analyzed using the shrink database 240 to ensure estimation of the shape and dimension of the pattern before shrink. This makes it possible to provide the CD-SEM apparatus capable of estimating the pattern shape and dimension with high accuracy.

The CD-SEM images derived from measurement of an arbitrary point of the pattern on the sample once or multiple times using the CD-SEM apparatus shown in FIG. 2 are used for analytical process through the shrink database. The sequence including the measurement condition for acquiring the CD-SEM image is stored in the memory 232 as a recipe to ensure measurement in accordance with the contents of the recipe. The recipe is allowed to set an arbitrary measurement condition sequence such as measurement at multiple points without being limited to the above-described measurement at the arbitrary points.

Figure 1:
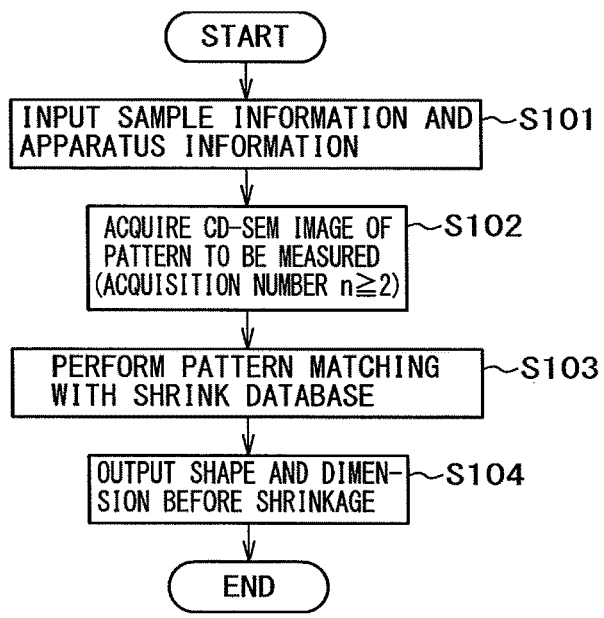
FIG. 1 is a flowchart representing a method of estimating a shape before shrink according to a first embodiment of the present invention.

The flow of the process according to the embodiment will be described based on FIG. 1 as an example for measuring an arbitrary pattern formed by the resist for ArF on the semiconductor substrate.

First, sample information and apparatus information are inputted (step S101). The sample information relates to the sample, for example, a sample title, a resist material, a design dimension of the pattern and the like. The item that can be inputted may only be entered. The apparatus information is the measurement condition, for example, accelerating voltage of the electron beam, current, scanning method, measurement magnification and the like.

Based on the measurement conditions by inputting the apparatus information, the CD-SEM acquires the CD-SEM image group with measured pattern (step S102). The ArF resist shrinks in the CD-SEM measurement. When acquiring multiple images by measuring the pattern to be measured at the same point multiple times using the CD-SEM, multiple CD-SEM images each with different shrink quantity may be obtained.

For example, assuming that the measurement condition includes the electron beam energy set to 500 V, current set to 8 pA, magnification set to 200000×, and the number of electron beam irradiations set to 4, 8, 16, 32 and 64, respectively, the images integrated by the respective number of electron beam irradiations are acquired.

Preferably, the measurement conditions for the multiple CD-SEM measurements are contained in the CD-SEM measurement condition obtained upon formation of the shrink database. The image feature amount such as the line profile is derived from the acquired multiple CD-SEM images.

The preliminarily formed shrink database and the multiple CD-SEM images obtained in step S102 are subjected to a pattern matching (collation) process (step S103). It is possible to subject the image feature amount such as the line profile derived from the multiple CD-SEM images obtained in step S102 and the shrink database to the pattern matching process.

The pattern matching process is executed by applying the CD-SEM image group of the measured pattern and the feature amount thereof to the shrink model and the correlation model between the CD-SEM image and the cross-sectional shape in the shrink database so that the shape and dimension of the measured pattern before shrink are estimated.

The shape and dimension of the measured pattern before shrink derived from the matching process are outputted (step S104). It is possible to display the image of the pattern shape in two-dimension or three-dimension, or both in two-dimension and three-dimension. As the dimension of the pattern, the resist height, width at each height of the resist, round shape at the upper part, trailing shape at the lower part, and a taper angle may be outputted and displayed in accordance with an operator's request.

Figure 9:
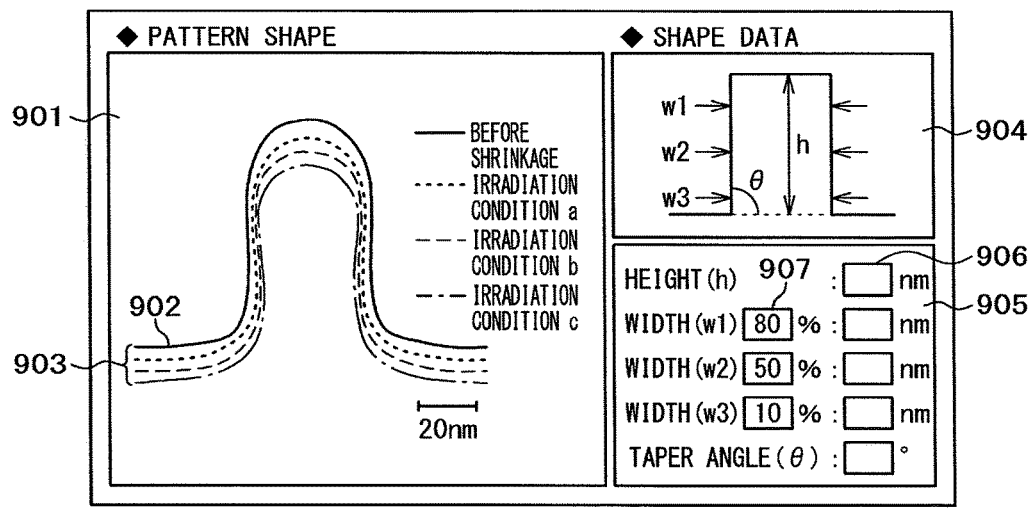
FIG. 9 is a view illustrating an exemplary output screen of the CD-SEM apparatus according to the first embodiment of the present invention.

FIG. 9 shows an example of the output screen. A pattern shape display (901) displays a pattern shape before shrink (902), and a pattern shape after shrink (903) corresponding to the CD-SEM image of the measured pattern acquired in step S102. Referring to FIG. 9, the pattern shape before shrink and multiple pattern shapes after shrink are overlaid. However, the display is not limited to the aforementioned mode. It is possible to display the respective pattern shapes individually. It is also possible to display the pattern shape in three-dimension, or both in two-dimension and three-dimension.

A length measurement display (905) displays the pattern shape represented by numerical values (906), for example, the resist height, the width at the arbitrary resist height, and the taper angle. The length measurement position of the resist width is inputted to a designated section (907) at which the rate to the resist height is entered so as to output the value of the width at the resist height desired to be measured. The number of the measurement positions of the resist width is not limited to 3. A schematic diagram (904) of the measurement position may also be displayed for easy identification of the measurement position.

The aforementioned flow allows estimation and output of the shape and dimension before shrink, which cannot be observed by the CD-SEM.

The shrink database will be described referring to FIGS. 3A and 3B.

Figure 3A:
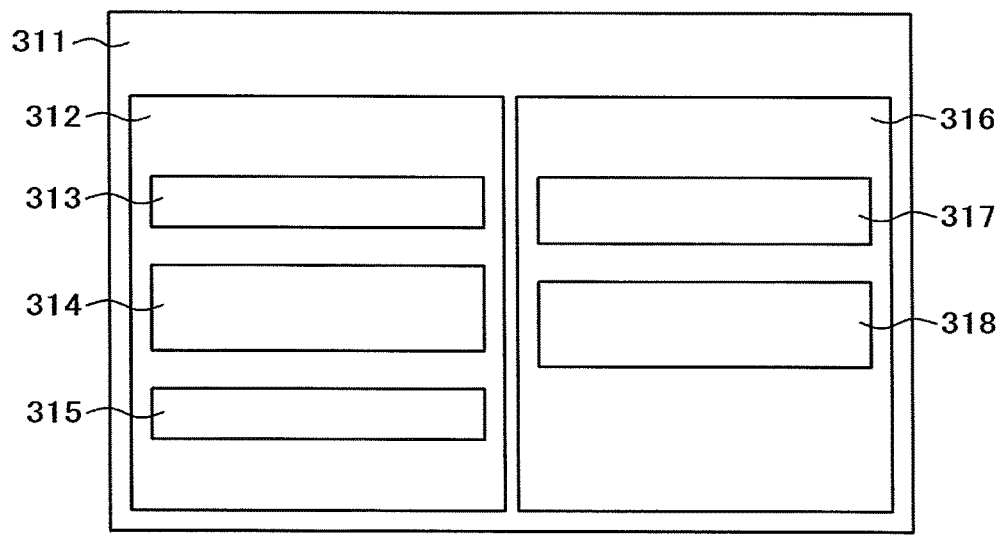
FIG. 3A is an explanatory view of a shrink database of the CD-SEM apparatus according to the first embodiment of the present invention.

FIG. 3A represents an exemplary structure of the shrink database. The shrink database (311) includes a data group (312) and a model (316).

The data group (312) is composed of the respective data including a cross-sectional shapes before electron beam irradiation (313), cross-sectional shapes under various electron beam irradiation conditions (314), and CD-SEM images (315) under various electron beam irradiation conditions. The model (316) is composed of the shrink model (317) and the correlation model (318) between the feature amount of the CD-SEM image and the cross-sectional shape.

The model (316) is generated based on the data group (312). The shrink model (317) is generated by modeling the relationship between the electron beam irradiation amount and the amount of change in the shape owing to shrink. The correlation model (318) between the CD-SEM image feature amount and the cross-sectional shape is generated by modeling the relationship between the feature amount of the CD-SEM image and the cross-sectional shape of the pattern. This allows estimation of the cross-sectional shape from the CD-SEM image. The use of the model (316) allows estimation of the cross-sectional shape and dimension before shrink with respect even to the electron beam irradiation conditions and the resist shape which are not contained in the data group (312).

According to this embodiment, the elements that form the data group are shown with respect to the cross-sectional shape before electron beam irradiation, cross-sectional shape under various electron beam irradiation conditions, and the CD-SEM images under various electron beam irradiation conditions. Furthermore, it is possible to add any other data.

According to this embodiment, the element for constituting the model is represented by taking two models of the shrink model and the correlation model between the CD-SEM image and the cross-sectional shape as the example. Furthermore, the model is not limited to the one as described above.

Figure 3B:
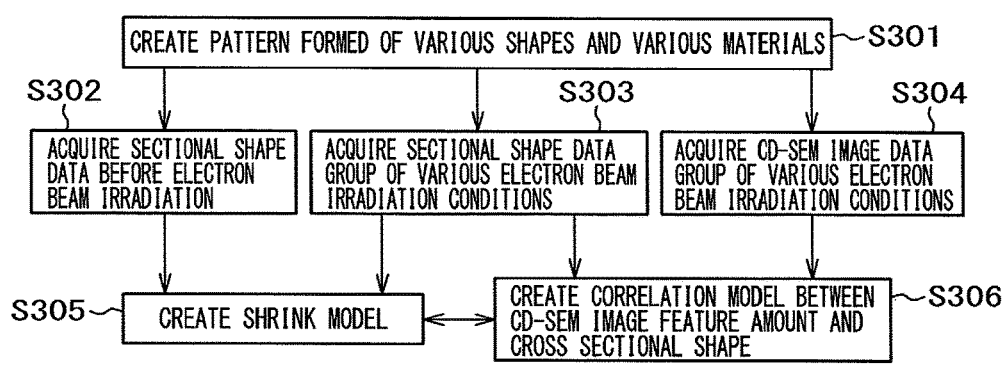
FIG. 3B is an explanatory view of procedures for generating a shrink model and a correlation model between a feature amount of the CD-SEM image and a cross-sectional shape in the shrink database as shown in FIG. 3A.

FIG. 3B represents an example of the flow for forming the shrink database. The patterns formed of various materials with various shapes are provided for forming the shrink database (step S301). The various shapes are provided by changing one or more of the width and height of the resist, the round shape at the upper part, the trailing shape at the lower part, and the taper angle. The various materials include the resist for ArF.

Data of the cross-sectional shape of the pattern before electron beam irradiation prepared in step S301 are acquired through STEM observation of the cross-section of the pattern (step S302).

The CD-SEM image data group of the pattern prepared in step S301 under various electron beam irradiation conditions is obtained (step S304). The image feature amount such as the line profile is derived from the obtained CD-SEM image. The electron beam irradiation condition includes the electron beam irradiation energy set to 500 V, electron beam current set to 8 pA, magnification set to 200000×, and the number of electron beam irradiations set to 2, 4, 8, 16, 32 and 64. The CD-SEM images with different electron beam irradiation amounts are acquired. Those images exhibit different shrink quantity so that the difference in the shrink trend owing to the difference in the shape and the material may be acquired as data. The specific values of the electron beam irradiation energy, current, magnification and the number of irradiations are not limited to the aforementioned values as the example.

The cross-sectional shape data of the resist pattern subjected to the electron beam irradiation under the same condition as that of the CD-SEM image acquired in step S304 are obtained (step S303). Preferably, the measurement point in step S304 matches the one in step S303. However, the measurement point in step S304 does not necessarily match the one in step S303 so long as the electron beam irradiation conditions are the same. An example of the procedure in step S303 for observing the cross-sectional shape of the pattern at the point measured using the CD-SEM in step S304 will be described later.

The relationship between the electron beam irradiation amount and the amount of change in the shape caused by the shrink is quantitatively analyzed in reference to the cross-sectional shape of the pattern before shrink which is obtained in step S302, and the cross-sectional shape of the pattern after shrink having the different electron beam irradiation amount in step S303 so that the shrink model is generated (step S305). This model is obtained by modeling the shrink phenomenon caused by the CD-SEM observation. For example, in addition to the cross-sectional shape and dimension after CD-SEM observation, the use of the electron beam irradiation condition and the shape data as the initial value allows estimation of the cross-sectional shape and the dimension before shrink, which cannot be observed by the CD-SEM.

The CD-SEM images with different electron beam irradiation quantity acquired in step S304, the feature amount such as the line profile, and the cross-sectional shape of the patterns with electron beam irradiation quantity obtained in step S303, corresponding to the one in step S304 are quantitatively analyzed to generate the correlation model between the feature amount of the CD-SEM image of the pattern and the cross-sectional shape (step S306). The use of the correlation model allows estimation of the cross-sectional shape (cross-sectional shape after shrink) under the corresponding CD-SEM image measurement conditions from the CD-SEM images.

The cross-sectional shape data of the pattern after shrink derived from the correlation model in step S306, and the electron beam irradiation condition are applied to the shrink model in step S305 to allow estimation of the shape and dimension of the pattern before shrink.

This example shows the elements that constitute the shrink database, taking two models including the shrink model and the correlation model between the CD-SEM image and the cross-sectional shape as the example. However, arbitrary model may be employed without limitation.

This embodiment uses the STEM observation as the method for observing the cross-sectional shape of the pattern in steps S302 and S303. However, the use of any other observation method may provide the similar effects so long as the method does not cause the shrink through the measurement, for example, the atomic force microscope (AFM) and the like.

Following is the description with respect to the method for observing the cross-sectional shape of the pattern at the CD-SEM observation point in forming the shrink database in reference to the flowchart of FIG. 4 and the schematic view of FIG. 5. This embodiment represents an example of observing the cross-section of the pattern at the CD-SEM observation point through micro-sampling with the focusing ion beam (FIB) in the Z contrast mode of STEM.

The flow will be described referring to FIG. 4. The resist pattern is subjected to the CD-SEM observation (step S401). By setting the observation magnification to 200000× for observing the pattern of sub-nanometer, the region about 700 nm sq. is irradiated with the electron beam. The image is derived from irradiation 16 times while setting the observation magnification to 200000×, the electron beam irradiation energy to 500 V, and the irradiation current to 8 pA.

Thereafter, a hafnium oxide (HfO$_2$) film with thickness ranging from 0.5 nm to 3 nm is formed on the resist pattern through the atomic layer deposition method (ALD method) (step S402). In FIB (Focused Ion Beam) microsampling, the protection film is generally formed for the purpose of protecting the surface from damage. If the protection film formed of the organic material such as carbon and resist is formed directly on the resist pattern, each of the resist pattern and the protection film formed of the light element exhibits substantially the same contrast in Z contrast image of STEM. This may make the boundary between the resist pattern and the protection film unclear. The HfO$_2$ film as the substance with higher atomic number than that of the material for forming the resist is employed as the boundary film applied onto the resist before formation of the protection film. This allows clear observation of the outline of the resist fringed with the HfO$_2$ in the form of the Z contrast image of STEM.

The ALD (Atomic Layer Deposition) method is employed for forming the thin film by atomic layer as a unit, exhibiting step coverage, uniform thickness, and high film thickness control performance. Accordingly, the film with the uniform film thickness may be formed on the side wall and the bottom part of the resist pattern, thus providing the outline of the resist with high accuracy.

Generally, the HfO$_2$ film is formed at approximately 300° C. The film formed at 100° C. has larger impurity content than that of the film formed at 300° C. However, it is confirmed to have sufficient contrast ratio derived from the STEM-Z contrast mode for the resist and the carbon protection film. The resist is generally subjected to the heat treatment called post baking at the temperature from 120° C. to 150° C. approximately after development. Formation of the HfO$_2$ film at 100° C. lower than 120° C. gives no thermal damage to the resist.

The carbon film is formed on the resist pattern covered with the HfO$_2$ film through the deposition method as a first protection film in the FIB processing (step S403). The thickness of the carbon film is set to the value varying from the one capable of protecting the resist pattern in formation of a second protection film (step S404) to the one sufficient to confirm the processed pattern point. For example, the film thickness may be set to 150 nm.

In step S401, a tungsten film with thickness of approximately 1 μm is formed on the region that contains the point subjected to the CD-SEM observation in step S401 as the second protection film (step S404). The film is formed onto the specific point in the FIB apparatus so that the CD-SEM observation point is located. At this time, it is possible to put a mark such as the line onto the thus formed tungsten film with the FIB for locating the CD-SEM observation point.

The region that contains the CD-SEM observation point is processed into a STEM sample through microsampling with the FIB (step S405). The use of the FIB microsampling method allows observation of the cross-section of the specific point of the sub-micron region. The cross-section of the point that has been observed with the CD-SEM may be observed. In other words, the CD-SEM image and the cross-sectional shape may be in one-to-one correspondence.

Formation of the STEM sample in the region which includes both the CD-SEM observed point (in this embodiment, 700 nm) and the CD-SEM unobserved point makes it possible to observe the cross-sectional shapes before and after the CD-SEM observation in the same STEM sample.

The thickness of the sample for the STEM observation is set to be in the range from 200 nm to 500 nm. The region irradiated with the electron beam in step S401 has a size about 700 nm sq., which is sufficiently large relative to the film thickness of the STEM sample.

The FIB process is executed to scrape the sample using the highly accelerated ion beam, and generally, the damage is given to the depth up to approximately 20 nm from the processed surface (in this case, the resist cross-section). The observation of the cross-section of the resist does not cover the grid image. Therefore, the thickness of the sample does not have to be reduced. The film thickness of the sample to be observed is made relatively thick to 200 nm or larger, making the ratio of the damage layer to the observation region less than 20 percent. The influence of the damage caused by the FIB processing is thought to be negligibly small.

The STEM observation of transmission type provides the image having integrated dispersion in the shape of the resist in the sample film thickness. If the STEM sample has an excessively large thickness, the boundary film is observed to have apparently larger thickness owing to the dispersion in the resist shape, thus causing the error in the obtained shape. It is therefore preferable to set the film thickness up to approximately 500 nm.

The cross-section of the sample produced in step S405 is observed in the Z contrast mode of STEM to acquire the cross-sectional STEM-Z contrast image (step S406). The Z contrast image of STEM is acquired by subjecting only transmission electron with large scattering angle to the film formation in the dark field observation of the STEM. The image contrast depends on the atomic number (Z) (in proportion to a square of Z). The observation with the higher resolution at approximately 1 nm may be performed, thus ensuring measurement of the resist shape with high accuracy.

In the case where the protection film formed of the organic material such as carbon and resist is directly formed on the resist pattern, the resist pattern and the protection film each formed of the light element have substantially the same contrasts in the form of the Z contrast images, thus making the boundary therebetween unclear. The use of the HfO$_2$ film on the resist as the substance with the larger atomic number than that of the material for forming the resist allows observation of the boundary film as the high contrast outline of the resist.

The cross-sectional TEM observation is employed as the measurement method conducted by irradiating the sample with the electron beam in the same manner as the CD-SEM. As this observation exhibits the higher accelerating voltage in observation than the CD-SEM, and the thickness that allows transmission of the electron beam (for example, approximately 200 nm), the electron irradiated upon the TEM observation transmits without remaining inside the resist. Therefore, the STEM observation provides the advantage that no resist shrink occurs as seen in observing the CD-SEM.

The resist outline is extracted from the STEM-Z contrast image of the cross-section obtained in step S406, with which the two dimensional data are formed (step S407). As the high-contrast boundary film ($HfO_2$) is formed at the boundary between the resist and the protection film, the image is binarized to trace the boundary film, thus allowing extraction of the outline. Various types of programs and software may be employed for extraction of the outline.

The aforementioned embodiment ensures observation of the cross-sectional shape of the same point as the one observed with the CD-SEM as well as formation of the shrink database.

This embodiment describes an example that the single position is irradiated with the electron beam under the single electron beam irradiation condition in step S401. Multiple points may be observed under the single electron beam irradiation condition, or the region having the multiple points observed under the multiple different electron beam irradiation conditions may be processed into the single or multiple STEM samples. The method allows the STEM observation of the shape in the single sample under the multiple electron beam irradiation conditions, thus ensuring reduction in the working hours. The method allows the study with respect to the change in the same sample, which makes it possible to achieve the measurement with higher accuracy under no influence of dispersion among the samples.

This embodiment describes the example using the $HfO_2$ film as the boundary film. However, the similar effect may be obtained by using the film other than the $HfO_2$ film so long as the Z contrast image of STEM provides the contrast ratio to the resist. Arbitrary film forming method may be applied without being limited to the ALD method so long as the method is intended to form the film on the side wall and the bottom part of the resist pattern.

This embodiment employs the carbon film as the first protection film. The similar effect may be obtained by using the substance that provides the contrast at the level similar to that of the resist in the Z contrast image of STEM, for example, the resist and $Al_2O_3$. Besides the deposition method, arbitrary film forming method may be applied so long as the resist is not damaged.

Figure 5A:
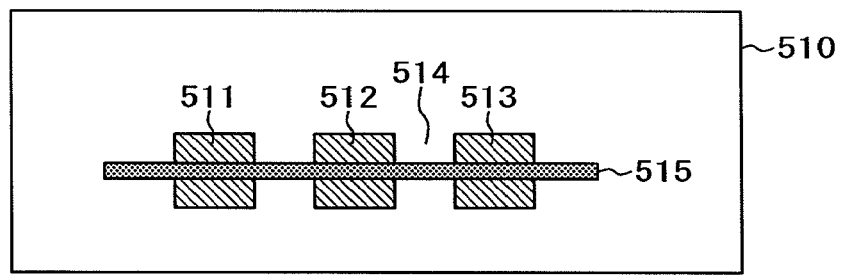
FIG. 5A is a plan view of an example of a sample used in the first embodiment of the present invention.

A supplementary explanation will be made with respect to the method of observing the cross-section according to the embodiment using the schematic view of the cross-section observation with the STEM shown in FIG. 5. FIG. 5A shows an example of a positional relationship between electron beam irradiation regions 511, 512, 513, and the STEM observation sample 515 with the film thickness reduced by the FIB in the resist sample 510. The resist pattern is formed in a direction vertical to the electron beam unirradiation region 514 through the FIB.

The electron beam irradiation condition includes the observation magnification set to 200000×, electron beam irradiation energy set to 500 V, and the number of electron beam irradiations set to 64, 2, and 16 to the electron beam irradiation regions 511, 512 and 513. The electron beam irradiation region has the size of 700 nm sq. approximately. Each interval between adjacent electron beam irradiation regions 511 and 512, and 512 and 513 is set to 500 nm. Each of the electron beam irradiation regions 511, 512 and 513 has the shape changed owing to the shrink. Accordingly the position may be confirmed with the optical microscope. The electron beam irradiation condition is not limited to those described in the embodiment. The number of the irradiation points, arrangement and size may be arbitrarily set to be fit with the STEM sample to be processed through the FIB.

The region including the electron beam irradiation regions 511, 512, 513, and the electron beam unirradiation region 514 is FIB processed to produce the STEM observation sample 515. This makes it possible to observe the different regions under the electron beam irradiation condition and the electron beam unirradiation region in the single STEM sample.

Figure 5B:
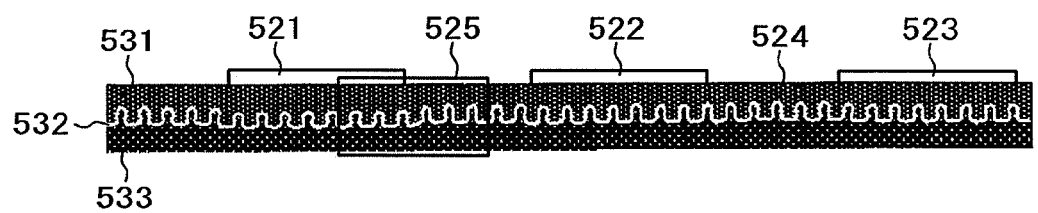
FIG. 5B is a schematic view illustrating a cross-section of the sample shown in FIG. 5A, which is observed with STEM.
Figure 5C:
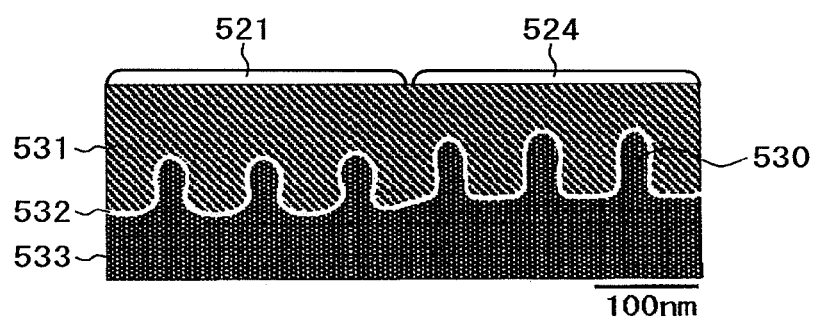
FIG. 5C is an enlarged view of an essential part of the schematic sectional view of FIG. 5B.

FIGS. 5B and 5C are schematic views of the STEM-Z contrast image. The cross-section of the electron beam unirradiation region 514 corresponds to the cross-section of a unirradiation region 524. The cross-section of the electron beam irradiation region 511 corresponds to a region 521. The cross-section of the electron beam irradiation region 512 corresponds to a region 522. The cross-section of the electron beam irradiation region 513 corresponds to a region 523.

The Z contrast image exhibits the contrast depending on the atomic number (Z). Therefore the difference in the contrast between the carbon deposition film (carbon protection film) 531 and a resist 530 which have close atomic numbers is small. Meanwhile, the boundary film ($HfO_2$) 532 contains the element with the atomic number larger than that of the resist 530 and the carbon protection film 531, resulting in high contrast (white) observation. The use of the $HfO_2$ film 532 as the boundary film allows clear observation of the outline of the resist 530.

FIG. 5C is an enlarged view of an expanded region 525 shown in FIG. 5B. The resist shape as the cross-section 521 in the electron beam irradiation region has the constriction around the center of the resist rather than the shrink shape similar to that of the resist as the cross-section 524 in the unirradiation region. An antireflection film 533 at the lower part of the resist 530 shrinks in the electron beam irradiation region (corresponding to 521). In this embodiment, the antireflection film is provided as an example. However, the use of such film is not necessarily required depending on the resist material, the film thickness and the wavelength of the exposing light.

The shapes of the resist and the antireflection film are deformed under the electron beam irradiation. A mere extrapolation of the shrink curve has still difficulty in highly accurate estimation of the shape before shrink. It is therefore essential to study on the correlation between the CD-SEM image and the cross-sectional shape, and change in the shrink shape under the electron beam irradiation for the purpose of estimating the shape before shrink. This embodiment allows observation of the cross-sectional shape at the point observed with the CD-SEM without causing any damage, and ensures to form the shrink database with high accuracy.

Figure 5D:
FIG. 5D is a view illustrating a resist outline in the schematic sectional view of FIG. 5C.

FIG. 5D represents an example of an outline 540 of the resist fringed with the boundary film ($HfO_2$) 532 shown in FIG. 5C. Extraction of the resist shape as the two-dimensional data of X and Y allows quantitative evaluation of the resist shape, ensuring formation of the shrink database.

Figure 6A:
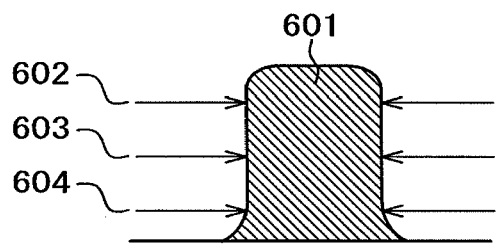
FIG. 6A is a schematic view illustrating a cross-sectional shape of the resist formed on the sample used in the first embodiment of the present invention.
Figure 6B:
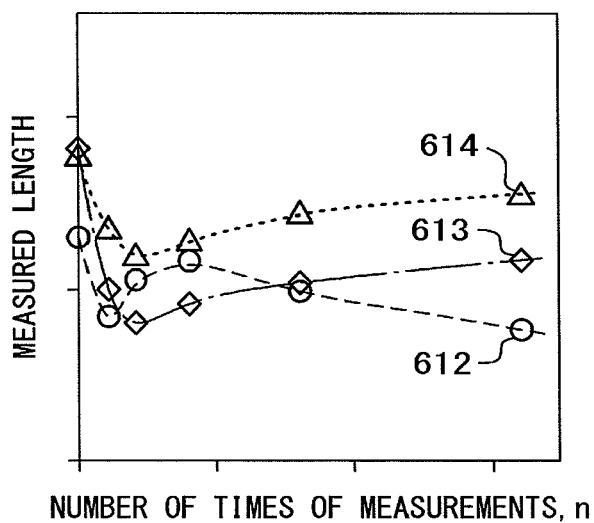
FIG. 6B is a view representing dependency of the resist on the number of measurements of the resist shape as shown in FIG. 6A.

FIGS. 6A and 6B show an example of dependency of the length measurement value of the resist shape on the number of measurements of the length of the resist shape by applying the method for observing the cross-sectional shape according to the embodiment. FIG. 6A is a schematic view of the cross-sectional shape of the resist, and FIG. 6B is a graph representing the dependency of the length measurement value on the number of measurements. Referring to the graph, each change of the length measurement values of the resist width of an upper part 602, an intermediate part 603, and a lower part 604 of the resist pattern 601 is represented by 612 ○, 613 ◇ and 614 △. The cross-sectional shape may be quantitatively evaluated, which allows expression of the relationship between the length measurement value and the number of measurements (electron beam irradiation quantity) by a function. Besides the resist width shown in FIG. 6, the relationship between the number of measurements (electron beam irradiation quantity) and change in the resist height, the taper angle, the round shape, the trailing shape or the like may be expressed by the function. The relationships expressed by those functions are allowed to constitute the shrink model of the shrink database.

The aforementioned method is employed for forming the shrink database to estimate the shape of the resist pattern before shrink using the CD-SEM apparatus shown in FIG. 2, and compare the estimated resist pattern shape before shrink with the base pattern shape upon dry etching using the resist pattern as the mask. The comparison result shows the good correlation.

The present embodiment ensures to provide the method for estimating the shape before shrink and the CD-SEM apparatus utilizing the shrink database, which allow highly accurate estimation of the pattern dimension before shrink when measuring the shape and dimension of the pattern formed of the shrinkable material under the electron beam irradiation through the CD-SEM.

Second Embodiment

A second embodiment will be described based on FIGS. 7 and 10, explaining an example of measuring multiple points of an arbitrary pattern formed of the resist for ArF on the semiconductor substrate. The explanation of the first embodiment, which is omitted herein is applicable to this embodiment unless otherwise specified.

FIG. 7 is a flowchart representing the method for estimating the shape before shrink according to this embodiment. The shape data of the measured pattern as the initial value are acquired. First, the sample information and apparatus information are inputted (step S111). The sample information relates to the sample, for example, sample title, resist material, pattern design dimension and the like. Only the item that can be inputted may be entered. The apparatus information is the measurement condition such as the accelerating voltage of the electron beam, current, scanning method, and measurement magnification.

Based on the measurement condition inputted as the apparatus information, the CD-SEM acquires the CD-SEM image group of the measured pattern used as the initial value (step S112). The ArF resist shrinks in the CD-SEM measurement. The same point of the measured pattern is subjected to multiple CD-SEM measurements so that multiple CD-SEM images are acquired. The resultant multiple CD-SEM images have different shrink quantity. For example, the measurement condition includes the electron beam energy set to 500 V, current set to 8 pA, magnification set to 200000×, and the number of electron beam irradiations set to 4, 8, 16, 32 and 64 to acquire the image integrated by the number of times of electron beam irradiations.

Preferably, the conditions for the multiple CD-SEM measurements are included in the CD-SEM measurement condition obtained upon formation of the shrink database. Each feature amount of the images such as the line profile is derived from the acquired multiple CD-SEM images. The CD-SEM images and the line profiles are stored in the memory.

The preliminarily formed shrink database and the multiple CD-EM images acquired in step S112 are subjected to a pattern matching process (step S113). It is possible to subject the image feature amounts such as the line profiles derived from the multiple CD-SEM images obtained in step S112 and the shrink database to the pattern matching process. In executing the pattern matching process, for example, the CD-SEM image group of the measured pattern and feature amount thereof are applied to the shrink model, and the correlation model between the CD-SEM image and the cross-sectional shape of the shrink database to estimate the shape and dimension of the measured pattern before shrink. It is possible to display the image of the pattern shape in two-dimension or three-dimension, or both in two-dimension and three-dimension. It is possible to output and display the resist height, the width at each height of the resist, the round shape at the upper part, the trailing shape at the lower part, and the taper angle as the pattern dimension in accordance with the operator's request.

Data of the shape and dimension of the measured pattern before shrink, which are derived from the pattern matching are inputted as the initial value of the sample information (step S114). If the initial value of the inputted sample information is different from the sample information inputted in step S111, the information is replaced with the one inputted in step S114. The pattern shape data as the initial values may be inputted in step S114. This allows the accurate estimation irrespective of the sample with indistinct sample information.

The stage is moved to the measured pattern at the position different from that of the measured pattern in step S112 (step S115). In step S115, the movement is to be made from the pattern measured in step S112 to another measured pattern. Therefore, beam deflection may be used for such movement without moving the stage. If the sample is generated in the same process step as the one used for the pattern measured in step S112, the sample may be replaced.

A single CD-SEM image of the measured pattern at the position different from the position in step S112 is acquired (step S116). The image feature amount such as the line profile is derived from the acquired CD-SEM image so that the CD-SEM image and the line profile are stored in the memory. The measurement conditions include the electron beam energy set to 500 V, current set to 8 pA, magnification set to 200000×, and the number of electron beam irradiations set to 16. However, any other measurement condition may be applied.

The initial value of the pattern shape inputted in step S114, the CD-SEM images acquired in step S116 and the feature amount of the image are subjected to the matching process with the shrink database (step S117). The matching process is executed under the condition that the initial value of the pattern shape is given. Therefore, the process is expected only for adjusting deviation from the initial value.

The shape and dimension of the measured pattern before shrink, which are derived from the matching process are outputted (step S118). The pattern shape may be displayed on the screen in two-dimension or three-dimension, or both in two-dimension and three-dimension. It is possible to output and display the resist height, the width of the resist at each height of the resist, the round shape at the upper part, the trialing shape at the lower part, and the taper angle as the pattern dimension in accordance with the operator's request.

In step S119, it is determined whether the measurement is to be finished or continued. When measuring the multiple measured patterns, the process steps from S115 to S118 are repeatedly executed to output each shape and dimension of the multiple measured patterns before shrink. The number of the measured patterns (number of repetitions) and designation of the measurement point may be inputted in step S111 or set as the sequence of the measurement condition.

The initial value of the sample information is inputted in step S114. Even if the single CD-SEM image of the measured pattern is only acquired in step S116, the matching process with the shrink database may be sufficiently executed in step S117. This makes it possible to reduce the measurement time.

In step S116, the single CD-SEM image is acquired for reducing the measurement time. However, multiple CD-SEM images with different numbers of electron beam irradiations may be acquired likewise the process in step S112. This makes it possible to estimate the shape and dimension before shrink with higher accuracy in step S117.

Figure 10:
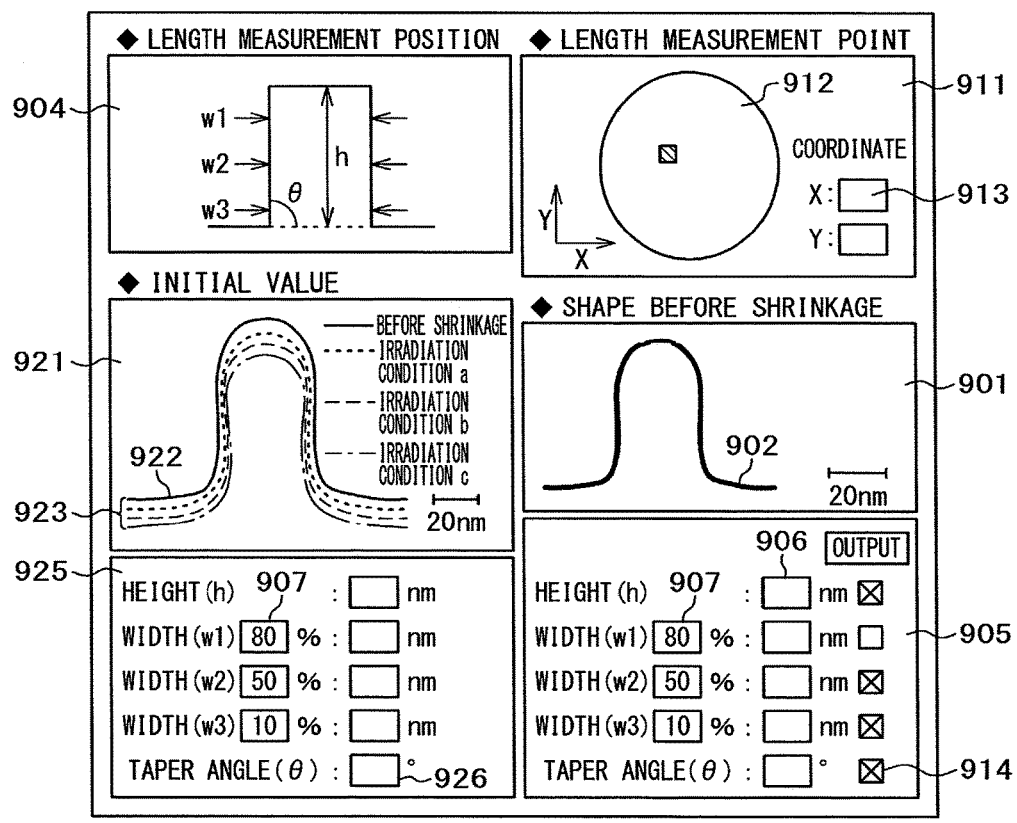
FIG. 10 is a view illustrating an exemplary output screen of the CD-SEM apparatus according to the second embodiment of the present invention.

FIG. 10 represents an example of the display screen. A pattern shape display (921) of the initial value displays a pattern shape before shrink (922) and a pattern shape after shrink (923) of the initial value corresponding to the CD-SEM image of the measured pattern acquired in step S112. FIG. 10 displays the pattern shape before shrink overlaid with multiple pattern shapes after shrink. However, the display mode is not limited to the one as described above. The respective pattern shapes may be displayed individually. The pattern shape may be three-dimensionally displayed, or displayed in both two-dimension and three-dimension.

A length measurement value display (925) of the initial value displays numerical values (926) of the pattern shape as the initial values such as the resist height, width at the arbitrary height of the resist, and the taper angle. The length measurement position of the resist width is entered in designated section (907) indicating the rate to the resist height to ensure output of the value of the width at the resist height desired to be measured. The number of length measurement positions of the resist width is not limited to 3. It is also possible to add a schematic diagram (904) illustrating the measurement position so as to be displayed for easy identification of the measurement position.

The chip or location to be measured is designated through a length measurement point designation display (911) among data of multiple measured patterns. It is possible to designate the location on a wafer map (912) and input length measurement point coordinates (913). If any one of the position and coordinates is changed on the wafer map, the other item is set to be adjusted to follow-up such change so that both values indicate the same location.

A pattern shape display (901) displays a pattern shape (902) before shrink at the location designated by the length measurement point destination display. It is possible to indicate the measurement position with the arrow on the pattern shape before shrink for easy identification of the measurement position. The pattern shape may be three-dimensionally displayed, or displayed both in two-dimension and three-dimension. If the multiple CD-SEM images with different number of electron beam irradiations are acquired in step S116, it is possible to add the pattern shape after shrink to the pattern shape display.

A length measurement value display (905) displays numerical values (906) of the pattern shape such as the resist height, width at the arbitrary height of the resist, and the taper angle. The measurement position of the resist width is entered in designated sections (907) indicating the rate to the resist height so as to ensure output of the resist width at the resist height desired to be measured. The number of the measurement positions of the resist width is not limited to 3. It is also possible to output the checked numerical values in the output selection part (914) as the wafer in-plane distribution and the text file of the numerical data.

The shrink database is formed through the aforementioned method to estimate the resist pattern shape before shrink using the CD-SEM apparatus shown in FIG. 2, and to compare the estimated resist pattern shape before shrink with the base pattern shape upon dry etching using the resist pattern as the mask. The comparison result shows good correlation.

This embodiment ensures to provide the method for estimating shape before shrink and the CD-SEM apparatus using the shrink database, which are capable of estimating the pattern dimension before shrink with high accuracy when measuring the shape and dimension of the pattern formed of the substance shrinkable under the electron beam irradiation. The use of the initial value of the sample information allows reduction in the measurement time.

Third Embodiment

A third embodiment will be described based on FIGS. 8 and 11, explaining an example of measuring multiple points of an arbitrary pattern formed of the resist for ArF on the semiconductor substrate. The explanation of the first or the second embodiment, which is omitted herein is applicable to this embodiment unless otherwise specified.

FIG. 8 is a flowchart representing the method for estimating the shape before shrink according to this embodiment. First, the apparatus information is inputted (step S121). The apparatus information is the measurement condition such as the accelerating voltage of the electron beam, current, scan method, and measurement magnification.

Then the sample information as the initial value of the measured pattern is inputted (step S122). The inputted information relates to the sample such as the sample title, the resist material, and the pattern design dimension. The information with reliability as high as possible is inputted, for example, the shape data of the measured pattern derived from the lithography simulator.

The single CD-SEM image of the measured pattern is acquired from the CD-SEM based on the measurement condition inputted as the apparatus information (step S123). The image feature amount such as the line profile is obtained from the acquired CD-SEM image. The CD-SEM image and the line profile are stored in the memory. The measurement condition includes the energy of the electron beam set to 500 V, current set to 8 pA, magnification set to 200000×, and the number of the electron beam irradiations set to 16. However, it is possible to apply another measurement condition.

The initial value of the pattern shape inputted in step S122, the CD-SEM image acquired in step S123 and the feature amount of the image are subjected to the matching process with the shrink database (step S124). The matching process is executed under the condition that the initial value of the pattern shape is given. Therefore, the process is expected only to adjust the deviation from the initial value.

In executing the pattern matching process, for example, the CD-SEM image group of the measured pattern and feature amount thereof are applied to the shrink model, and the correlation model between the CD-SEM image and the cross-sectional shape of the shrink database to estimate the shape and dimension of the measured pattern before shrink.

The shape and dimension of the measured pattern before shrink, which are obtained in step S124 are outputted (step S125). The pattern shape may be displayed on the screen in two-dimension or three-dimension, or both in two-dimension and three-dimension. It is possible to output and display the resist height, the width of the resist at each height of the resist, the round shape at the upper part, the trialing shape at the lower part, and the taper angle as the pattern dimension in accordance with the operator's request.

In step S126, it is determined whether the measurement is finished or continued. When measuring the multiple measured patterns, the process steps from S123 to S125 are repeatedly executed to output each shape and dimension of the multiple measured patterns before shrink. The number of the measured patterns (number of repetitions) and designation of the measurement point may be inputted in step S121 or set as the sequence of the measurement condition.

The initial value of the sample information is inputted in step S122. Even if the single CD-SEM image of the measured pattern is only acquired in step S123, the matching process with the shrink database may be sufficiently executed in step S124. This makes it possible to reduce the measurement time.

Figure 11:
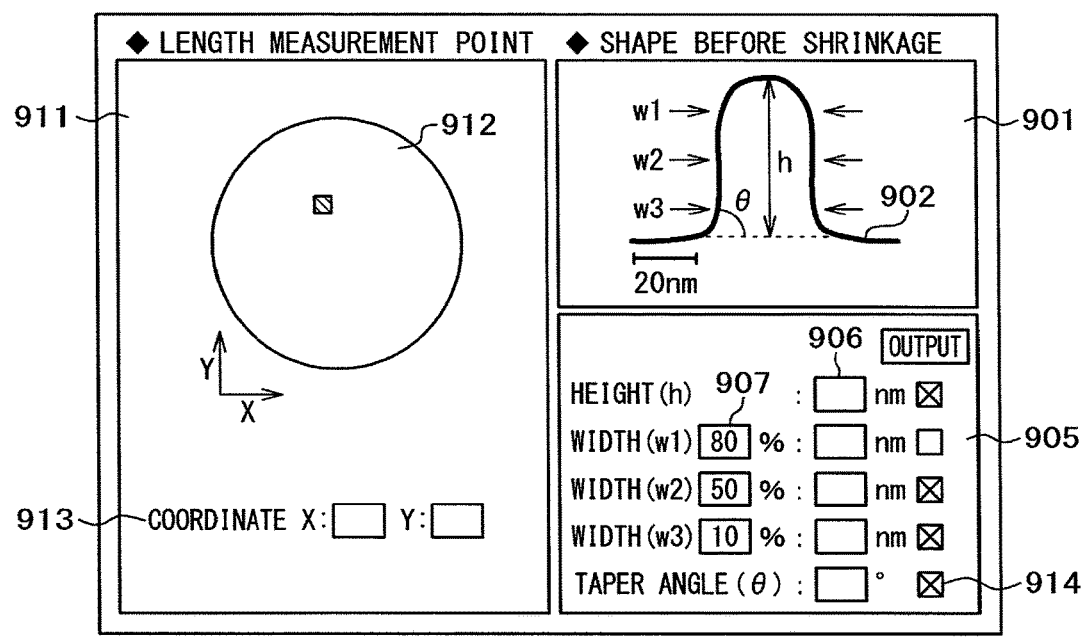
FIG. 11 is a view illustrating an exemplary output screen of the CD-SEM apparatus according to the third embodiment of the present invention.

An example of the output screen is shown in FIG. 11. The point desired to be measured is designated through the length measurement point designation display (911) among data of multiple measured patterns. It is possible to designate the location on the wafer map (912) and input the length measurement point coordinates (913). If any one of the position and coordinates is changed on the wafer map, the other item is set to be adjusted to follow-up such change so that both values indicate the same location.

The pattern shape display (901) displays the pattern shape (902) before shrink. It is possible to indicate the measurement position with the arrow on the pattern shape before shrink for easy identification of the measurement position. The pattern shape may be three-dimensionally displayed, or displayed both in two-dimension and three-dimension.

The length measurement value display (905) displays the numerical values (906) of the pattern shape such as the resist height, width at the arbitrary height of the resist, and the taper angle. The length measurement position of the resist width is entered in designated sections (907) indicating the rate to the resist height so as to ensure output of the resist width at the resist height desired to be measured. The number of the measurement positions of the resist width is not limited to 3. It is also possible to output the checked numerical values in the output selection part (914) as the wafer in-plane distribution and the text file of the numerical data.

The shrink database is formed through the aforementioned method to estimate the resist pattern shape before shrink using the CD-SEM apparatus shown in FIG. 2, and to compare the estimated resist pattern shape before shrink with the base pattern shape upon dry etching using the resist pattern as the mask. The comparison result shows good correlation.

This embodiment ensures to provide the method for estimating shape before shrink and the CD-SEM apparatus using the shrink database, which are capable of estimating the pattern dimension before shrink with high accuracy when measuring the shape and dimension of the pattern formed of the substance shrinkable under the electron beam irradiation. The use of the initial value of the sample information allows reduction in the measurement time.

The present invention is not limited to the embodiments as described above, and may include various modifications.

The embodiments have been described in detail for better understanding of the present invention, and are not necessarily restricted to the one provided with all the structures of the description. The structure of any one of the embodiments may be partially replaced with that of the other embodiment. Alternatively, it is possible to add the structure of any one of the embodiments to that of the other embodiment. It is also possible to have the part of the structure of the respective embodiments added to, removed from and replaced with the other structure.

REFERENCE SIGNS LIST

201 . . . electron gun, 202 . . . primary electron, 203 . . . condenser lens, 204 . . . aperture, 205 . . . deflection coil, 206 . . . objective lens, 207 . . . sample, 208 . . . sample stage, 220 . . . secondary electron, 221 . . . secondary electron detector, 222 . . . A/D converter, 510 . . . sample, 311 . . . shrink database, 312 . . . data group, 316 . . . model, 511 . . . electron beam irradiation region, 512 . . . electron beam irradiation region, 513 . . . electron beam irradiation region, 514 . . . electron beam unirradiation region, 515 . . . STEM observation sample, 521 . . . cross-section of electron beam irradiation region 511, 522 . . . cross-section of electron beam irradiation region 512, 523 . . . cross-section of electron beam irradiation region 513, 524 . . . cross-section of electron beam unirradiation region, 525 . . . expanded region, 530 . . . resist, 531 . . . carbon protection film, 532 . . . boundary film ($HfO_2$), 533 . . . antireflection film, 540 . . . outline of resist, 601 . . . resist pattern, 602 . . . upper part of resist, 603 . . . intermediate part of resist, 604 . . . lower part of resist, 612 . . . change in measurement value at upper part of resist with respect to number of measurements, 613 . . . change in measurement value at intermediate part of resist with respect to number of measurements, 614 . . . change in measurement value at lower part of resist with respect to number of measurements, 901 . . . pattern shape display, 902 . . . pattern shape before shrink, 903 . . . pattern shape after shrink, 904 . . . schematic view of measurement position, 905 . . . display of a length measurement value, 906 . . . display of numerical values of pattern shape, 907 . . . section for designating ratio to resist height, 911 . . . display for designating a length measurement point, 912 . . . wafer map, 913 . . . coordinates of a length measurement point, 914 . . . output selection part, 921 . . . display of pattern shape of initial value, 922 . . . pattern shape of initial value before shrink, 923 . . . pattern shape of initial value after shrink, 925 . . . display of initial value of measurement value, 926 . . . display of numerical value of pattern shape as initial value.

The invention claimed is:

1. A method for estimating shape before shrink of a pattern used for measuring a shape and a dimension of the pattern formed of a substance which shrinks under an electron beam irradiation using a CD-SEM, the method comprising:
preparing a shrink database comprising a data group and a model based on said data group,
wherein the data group comprises cross-sectional shape data of the pattern formed of said substance before the electron beam irradiation, a cross-sectional shape data group obtained under various electron beam irradiation conditions, and a CD-SEM image data group obtained under various electron beam irradiation conditions, wherein the model comprises a shrink model generated by using the cross-sectional shape data of the pattern formed of said substance before the electron beam irradiation and the cross-sectional shape data group obtained under various electron beam irradiation conditions, and a correlation model between a CD-SEM image feature amount and a cross-sectional shape generated by using the cross-sectional shape data group obtained under various electron beam irradiation conditions and the CD-SEM image data group obtained under various electron beam irradiation conditions, and wherein the cross-sectional shape data comprises a plurality of resist widths each associated with a corresponding different resist height so as to form a 3D cross-sectional pattern used for measuring;

acquiring a CD-SEM image of a 3D cross-sectional pattern to be measured formed of said substance, wherein the 3D cross-sectional pattern is based on the plurality of resist widths and heights; and estimating and outputting a shape and a dimension of the 3D cross-sectional pattern to be measured before shrink using the CD-SEM image and data of the shrink database.

2. The method for estimating shape before shrink according to claim 1, wherein the shrink database includes data of the patterns with various shapes, which are formed of various substances.

3. The method for estimating shape before shrink according to claim 2, wherein the cross-sectional shape data before electron beam irradiation and the cross-sectional shape data group acquired under the various electron beam irradiation conditions which constitute the shrink database are obtained by processing the pattern into a cross-section sample through a converging ion beam processing method, and observing the cross-section sample with a transmission electron microscope.

4. The method for estimating shape before shrink according to claim 3, wherein a boundary film formed of a substance with larger atomic number than that of the substance for forming the pattern is further applied on a surface of the pattern, and a protection film is applied on the boundary film before the pattern is processed through the converging ion beam processing method.

5. The method for estimating shape before shrink according to claim 3, wherein the cross-section sample includes an electron beam irradiation region and an electron beam unirradiation region.

6. A CD-SEM apparatus comprising:
an electron beam source;
a sample stage on which a sample to be measured is disposed;
an electron optical system for irradiating the sample on the sample stage with an electron emitted from the electron beam source;
a control process unit for executing an image processing based on a secondary electron discharged from the sample; and
a shrink database which comprises
cross-sectional shape data of a pattern before electron beam irradiation, the pattern formed of a substance which shrinks under the electron beam irradiation;
a cross-sectional shape data group obtained under various electron beam irradiation conditions;
a CD-SEM image data group obtained under various electron beam irradiation conditions;
a shrink model generated using said cross-sectional shape data group using the cross-sectional shape data of the pattern formed of said substance before the electron beam irradiation and the cross-sectional shape data group obtained under various electron beam irradiation conditions; and
a correlation model which is generated using the cross-sectional shape data group obtained under various electron beam irradiation conditions and the CD-SEM image data group obtained under various electron beam irradiation conditions and which models a relationship between a CD-SEM image feature amount and a cross-sectional shape for estimating the shape of the pattern formed of the substance before shrink,
wherein the cross-sectional shape data comprises a plurality of resist widths each associated with a corresponding different resist height, said plurality of resist widths and heights being used to form said pattern as a 3D pattern formed of said substance before the electron beam irradiation.

7. The CD-SEM apparatus according to claim 6, wherein the shrink database includes data of the patterns with various shapes, which are formed of various substances.

8. The CD-SEM apparatus according to claim 7,
wherein the cross-sectional shape data before electron beam irradiation and the cross-sectional shape data group acquired under the various electron beam irradiation conditions which constitute the shrink database are obtained by processing the pattern into a cross-section sample through a converging ion beam processing method, and observing the cross-section sample with a transmission electron microscope.

9. The CD-SEM apparatus according to claim 8,
wherein a boundary film formed of a substance with larger atomic number than that of the substance for forming the pattern is further applied on a surface of the pattern, and a protection film is applied on the boundary film before the pattern is processed through the converging ion beam processing method.

10. The CD-SEM apparatus according to claim 9, wherein the shrink database is included in the control process unit.

11. The CD-SEM apparatus according to claim 9, further comprising a display unit connected to the control process unit for displaying the cross-sectional shapes before and after shrink of a measured pattern formed of the substance which shrinks under electron beam irradiation on the measured sample.

12. The CD-SEM apparatus according to claim 6, wherein each of said plurality of resist widths is associated with one of at least three resist heights comprising a first width at a height of an upper part of a resist pattern, a second width at a height of an intermediate part of the resist pattern, and a third width at a height of a lower part of the resist pattern.

13. The method for estimating shape before shrink according to claim 1,
wherein each of said plurality of resist widths is associated with one of at least three resist heights comprising a first width at a height of an upper part of a resist pattern, a second width at a height of an intermediate part of the resist pattern, and a third width at a height of a lower part of the resist pattern.

* * * * *